(12) United States Patent
LaValley et al.

(10) Patent No.: US 7,636,154 B1
(45) Date of Patent: Dec. 22, 2009

(54) MODULAR OPTICAL DETECTION SYSTEM FOR POINT AIRBORNE AND AREA SURFACE SUBSTANCE DETECTION

(75) Inventors: Howard N. LaValley, Albuquerque, NM (US); Robert Almassy, Alexandria, VA (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 340 days.

(21) Appl. No.: 11/614,676

(22) Filed: Dec. 21, 2006

(51) Int. Cl.
G01N 1/00 (2006.01)
G01N 33/28 (2006.01)
G01B 11/16 (2006.01)
G01J 3/40 (2006.01)

(52) U.S. Cl. ............... 356/73; 356/32; 356/302
(58) Field of Classification Search ........ 73/23.2, 73/28.01–28.05, 31.07; 356/72–73, 300–334, 356/402–425
See application file for complete search history.

(56) References Cited

U.S. PATENT DOCUMENTS

| | | | |
|---|---|---|---|
| 3,364,727 A * | 1/1968 | Heath | 73/19.01 |
| 4,164,138 A * | 8/1979 | Burkhart | 73/23.2 |
| 4,290,043 A * | 9/1981 | Kaplan | 340/984 |
| 4,447,800 A * | 5/1984 | Kasuya et al. | 340/904 |
| 4,555,627 A * | 11/1985 | McRae, Jr. | 250/334 |
| 4,689,052 A * | 8/1987 | Ogren et al. | 95/291 |
| 5,373,160 A * | 12/1994 | Taylor | 250/338.5 |
| 5,500,369 A * | 3/1996 | Kiplinger | 435/309.1 |
| 5,687,093 A * | 11/1997 | Long et al. | 703/1 |
| 5,932,818 A | 8/1999 | Novick et al. | |
| 6,694,266 B1 | 2/2004 | Jackson et al. | |
| 6,732,569 B2 * | 5/2004 | Ondov et al. | 73/28.05 |
| 6,765,668 B2 | 7/2004 | Gardner, Jr. et al. | |
| 6,777,228 B2 * | 8/2004 | Lejeune | 435/309.1 |
| 6,788,407 B1 | 9/2004 | Higdon et al. | |
| 6,847,446 B2 | 1/2005 | Shilling | |
| 6,852,527 B2 | 2/2005 | Chan et al. | |
| 6,865,196 B2 | 3/2005 | Dobbs et al. | |
| 6,865,926 B2 | 3/2005 | O'Brien et al. | |
| 6,893,876 B2 | 5/2005 | Perraut et al. | |
| 6,917,423 B2 | 7/2005 | Gardner, Jr. et al. | |
| 6,947,134 B2 * | 9/2005 | Chang et al. | 356/318 |
| 6,949,734 B2 | 9/2005 | Neff et al. | |
| 6,952,945 B2 | 10/2005 | O'Brien | |
| 6,985,818 B1 | 1/2006 | Samuels | |
| 7,009,170 B2 | 3/2006 | Dobbs et al. | |
| 7,012,249 B2 | 3/2006 | Krutchinsky et al. | |
| 7,113,275 B2 * | 9/2006 | Gardner et al. | 356/301 |

(Continued)

*Primary Examiner*—Gregory J Toatley, Jr.
*Assistant Examiner*—Jarreas C Underwood
(74) *Attorney, Agent, or Firm*—Edell, Shapiro & Finnan, LLC

(57) ABSTRACT

A detection system and method are provided having vehicle-mounted and manportable mobile surveillance capabilities with minimal equipment redundancy. The system comprises a vehicle-mounted sensor unit, a hand-held unit, a manportable unit and a vehicle-mounted air collector unit. The vehicle-mounted sensor unit comprises a spectroscopy subsystem that is configured to direct light onto a surface outside the vehicle and to capture scattered optical energy from the surface outside the vehicle while the vehicle is moving. The hand-held unit may be removably mounted to the air collector unit to interrogate airborne particles in collected air. The hand-held unit is removable from the air collector unit and is connected to the manportable unit by a cable so as to form an integrated portable detection system for mobile surveillance away from the vehicle by a user.

26 Claims, 11 Drawing Sheets

U.S. PATENT DOCUMENTS

| | | | |
|---|---|---|---|
| 7,271,387 B2 * | 9/2007 | Chou et al. | 250/341.1 |
| 7,342,214 B2 * | 3/2008 | Tuschel et al. | 250/208.1 |
| 7,400,405 B2 * | 7/2008 | Sadeghi et al. | 356/417 |
| 7,416,902 B2 * | 8/2008 | Pletcher et al. | 436/174 |
| 7,511,809 B2 | 3/2009 | Schneider et al. | |
| 2002/0031843 A1 | 3/2002 | Harmon | |
| 2003/0223063 A1 | 12/2003 | Hill et al. | |
| 2005/0105079 A1 | 5/2005 | Pletcher et al. | |
| 2005/0179893 A1 | 8/2005 | Hill | |
| 2005/0214168 A1 | 9/2005 | Lin et al. | |
| 2005/0229698 A1 * | 10/2005 | Beecroft et al. | 73/300 |
| 2005/0280814 A1 | 12/2005 | Iuliano | |
| 2006/0061762 A1 * | 3/2006 | Dwight et al. | 356/301 |

* cited by examiner

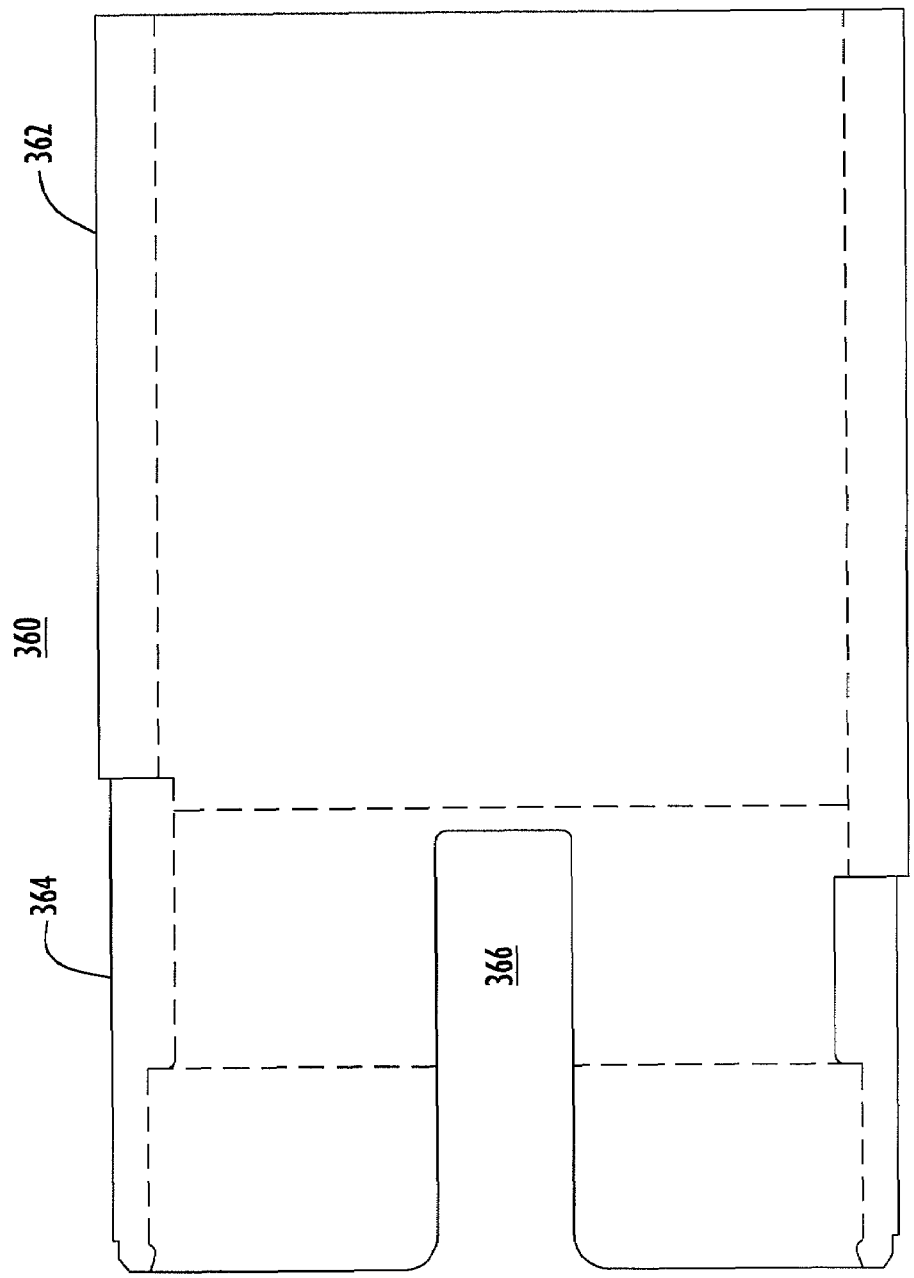

FIG. 11

MODULAR OPTICAL DETECTION SYSTEM FOR POINT AIRBORNE AND AREA SURFACE SUBSTANCE DETECTION

GOVERNMENT LICENSE RIGHTS

The U.S. Government may have a paid-up license in this invention and the right in limited circumstances to require the patent owner to license others on reasonable terms as provided for by the terms of contract Nos. W911SR-05-C-0015 and HSHQDC-06-0007.

BACKGROUND OF THE INVENTION

A body of technology has been developed for non-contact substance detection of substances. One application of this technology is to detect for the presence of a substance that is harmful to humans, whether intentionally or inadvertently deployed.

Spectroscopy is an example of a technology that is used to analyze the spectrum produced in response to illumination of a substance with a beam of light. For example, the beam of light may be in the ultraviolet wavelength region. The light beam interacts with the substance(s) surface and scatters back or returns optical energy in certain wavelength regions depending on the chemical or biological make-up of the substance(s). The returned optical energy is also referred to as the signature. In a spectroscopy-based detection system, the constituent wavelengths of the returned optical energy are separated out by a spectrograph and measured.

Raman spectroscopy is a spectroscopy technique useful to study vibrational, rotational, and other low-frequency modes in a system. Fluorescence spectroscopy is another response useful to discern characteristics of a substance. Fluorescence refers to emission of light caused when a material absorbs optical energy of one wavelength and re-emits light of another wavelength. Fluorescence spectroscopy has evolved into a powerful tool for the study of chemical, semiconductor, photochemical, and biochemical species.

One platform for deploying spectroscopy detection equipment is a manned or unmanned vehicle. On such a platform, it is desirable to minimize the amount of equipment needed to carry out the desired functions in order to conserve space, weight and power resources, but without sacrificing detection capabilities. Thus, whereas devices may be heretofore known that are each capable of performing a specific detection technique, what is needed is a detection system made of modules that use the same detection technologies and therefore can share many components for optimal deployment in a space-limited platform.

SUMMARY OF THE INVENTION

Briefly, a detection system and method are provided having vehicle-mounted and manportable mobile surveillance capabilities with minimal equipment redundancy. The system comprises a vehicle-mounted sensor unit, a hand-held unit, a manportable unit and a vehicle-mounted air collector unit. The vehicle-mounted sensor unit comprises a spectroscopy subsystem that is configured to direct light to a surface beneath the vehicle and to capture scattered optical energy from the surface beneath the vehicle while the vehicle is moving. The hand-held unit comprises a light source that emits a light beam onto a surface on which surface a substance to be analyzed may be present, and collection optics that captures scattered optical energy from the surface. The manportable unit connects to the hand-held unit to receive the scattered optical energy captured by the hand-held unit. The manportable unit further comprises a spectrograph that converts the captured scattered optical energy from the hand-held unit to spectrum data.

The vehicle-mounted air collector unit collects air and separates particles in the collected air for deposit onto a collection surface. The air collecting unit comprises a port to permit optical access to the collection surface by the hand-held unit and a support structure (e.g., a holster) that removably supports the hand-held unit in a position so that the light source in the hand-held unit can direct light onto the collection surface and the collection optics can capture scattered optical energy from the collection surface.

The hand-held unit is removable from the air collector unit to permit the manportable unit and the hand-held unit to be carried away from the vehicle for use as an integrated portable detection system by a user for mobile surveillance of surfaces outside of the air sampler, and/or away from the vehicle.

BRIEF DESCRIPTION OF THE DRAWINGS

FIG. 5B is a side view of a holster support device for the hand-held unit according to an embodiment of the invention.

FIG. 11 is a pictorial diagram showing the multiple capabilities of the system according to the invention.

DETAILED DESCRIPTION

The present invention is directed to a modular detection system capable of point airborne and area surface contamination detection. The system may be deployed on a manned or unmanned vehicle in one embodiment.

Figure 1:
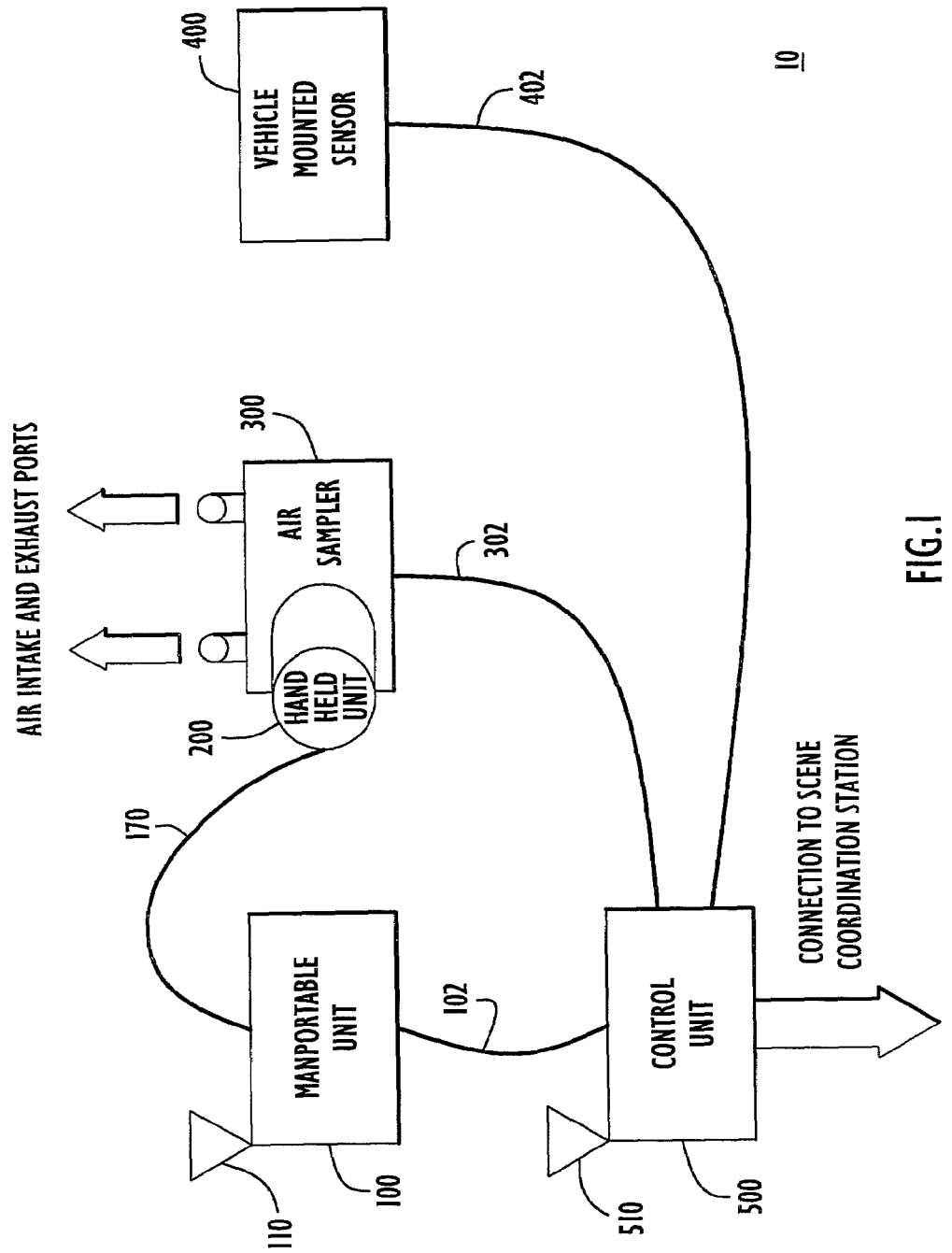
FIG. 1 is a block diagram of the system according to an embodiment of the invention.

Referring first to FIG. 1, the modular detection system according to the present invention is shown generally at 10 and comprises a manportable unit 100 and an associated hand-held unit 200 (also referred to herein as a "wand") an air sampler or collector unit 300, a vehicle mounted sensor unit 400 and a control unit 500. In one embodiment, the air sampler 300 and control unit 500 are mounted on the same vehicle as the vehicle-mounted sensor 400, and the air sampler 300 and the vehicle-mounted sensor 400 connect to the control unit 500 by wired connections 302 and 402, respectively. The manportable unit 100 may connect to the control unit 500 by a wired connection 102 or by a wireless link. For example, the manportable unit 100 may comprise an antenna 110 that is used for wireless communication with antenna 510 of the control unit 500. The control unit 500 may be in further communication, by wired or wireless link, with a remotely located scene coordination unit.

The manportable unit 100 and its associated hand-held unit 200 are useful for mobile contamination surface detection for surveillance and mapping capabilities. The air sampler 300 collects samples of air that may contain airborne contaminants in the form of aerosols or vapors. On the other hand, the vehicle-mounted sensor 400 is designed to scan a surface, such as a road or ground surface, from a vehicle to which it is mounted as the vehicle moves about. The units 100, 200, 300 and 400 have overlapping functions. The vehicle-mounted sensor 400 may be one that is already capable of remotely analyzing surfaces for various substances. An example of a detection system 400 is the LISA™ Raman detector manufactured and marketed by ITT Industries. The LISA™ Raman detector is capable of performing standoff or remote surface detection of solids and liquids. By employing a modular design, some of the common elements do not need to be duplicated, thereby increasing the efficiency of space, weight and power. In addition, system complexity can be reduced while expanding surveillance capabilities as will become apparent hereinafter.

One advantage of the air sampler module 300 is that it does not require integration of a new detection technique; it can be used with a proven manportable detection system (comprised of units 100 and 200) that is already in use for non-contact detection of substances on surfaces, thereby leveraging the same system to detect aerosols and vapor-sourced particles contained in collected air samples. Consequently, it is possible to search/scan for aerosols or vapors before liquid is on the ground and for vapors when no liquid will be detected on the ground.

Figure 2:
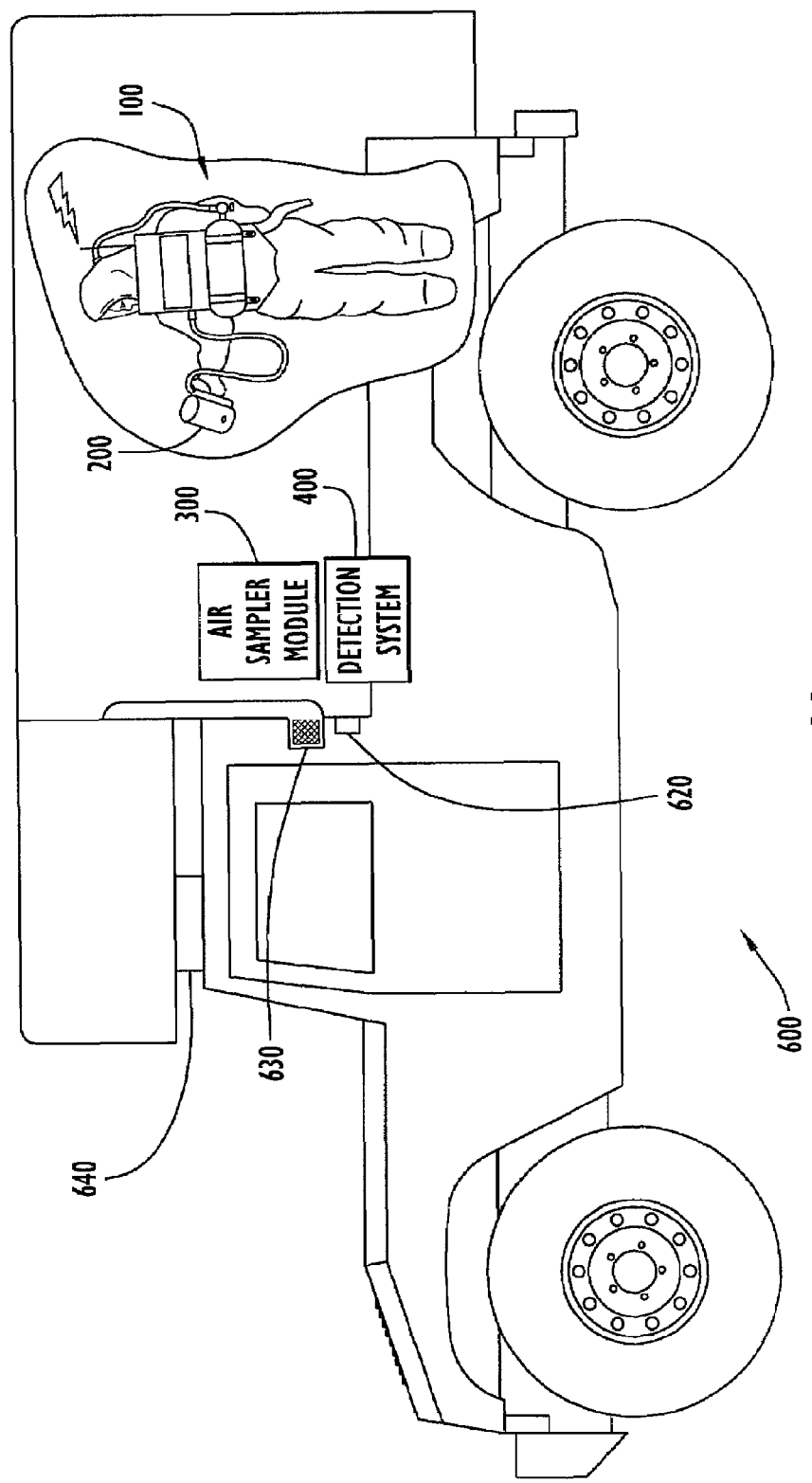
FIG. 2 is a block diagram of the system in association with a vehicle to which certain components of the system are mounted according to an embodiment of the invention.

Turning to FIG. 2, the system 10 is shown mounted on a vehicle 600 wherein the manportable unit 100 is being worn by a person who is also holding in his/her hand the hand-held unit 200. There is an input/output box 620 that holds a movable directional air intake vent 630 and an air return bellows 640. The movable directional air vent 630 is coupled to the intake port of the air sampler 300 and is used to capture air that is to be analyzed. The air return bellows 640 exhausts the air from the air sampler 300 to the atmosphere in such a manner as to avoid introducing the exhausted air back into the intake vent 630. A vehicle 600 equipped with a detection equipment shown in FIG. 2 provides for the capability of detecting substances (liquid and/or solid) by scanning a surface outside (e.g., beneath) the vehicle 600 and airborne substances in an environment while moving at relatively high speeds. The vehicle 600 may be a manned vehicle or an unmanned vehicle, and need not take the form of a car or truck. For example, the vehicle may be a robot or other mechanized mobile device that is capable of moving about a region and carrying the equipment described herein.

Figure 3:
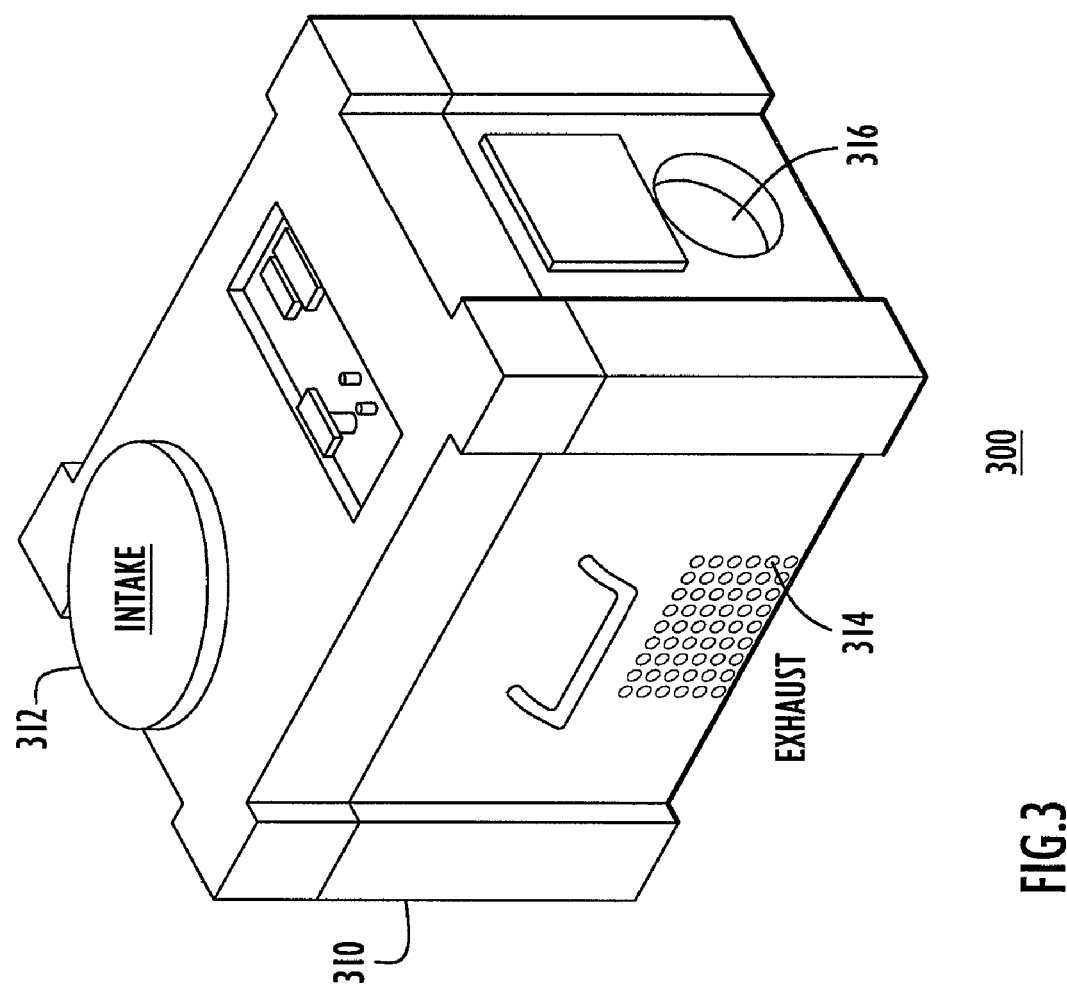
FIG. 3 is a perspective view of an air sampler unit used in the system according to an embodiment of the invention.
Figure 4:
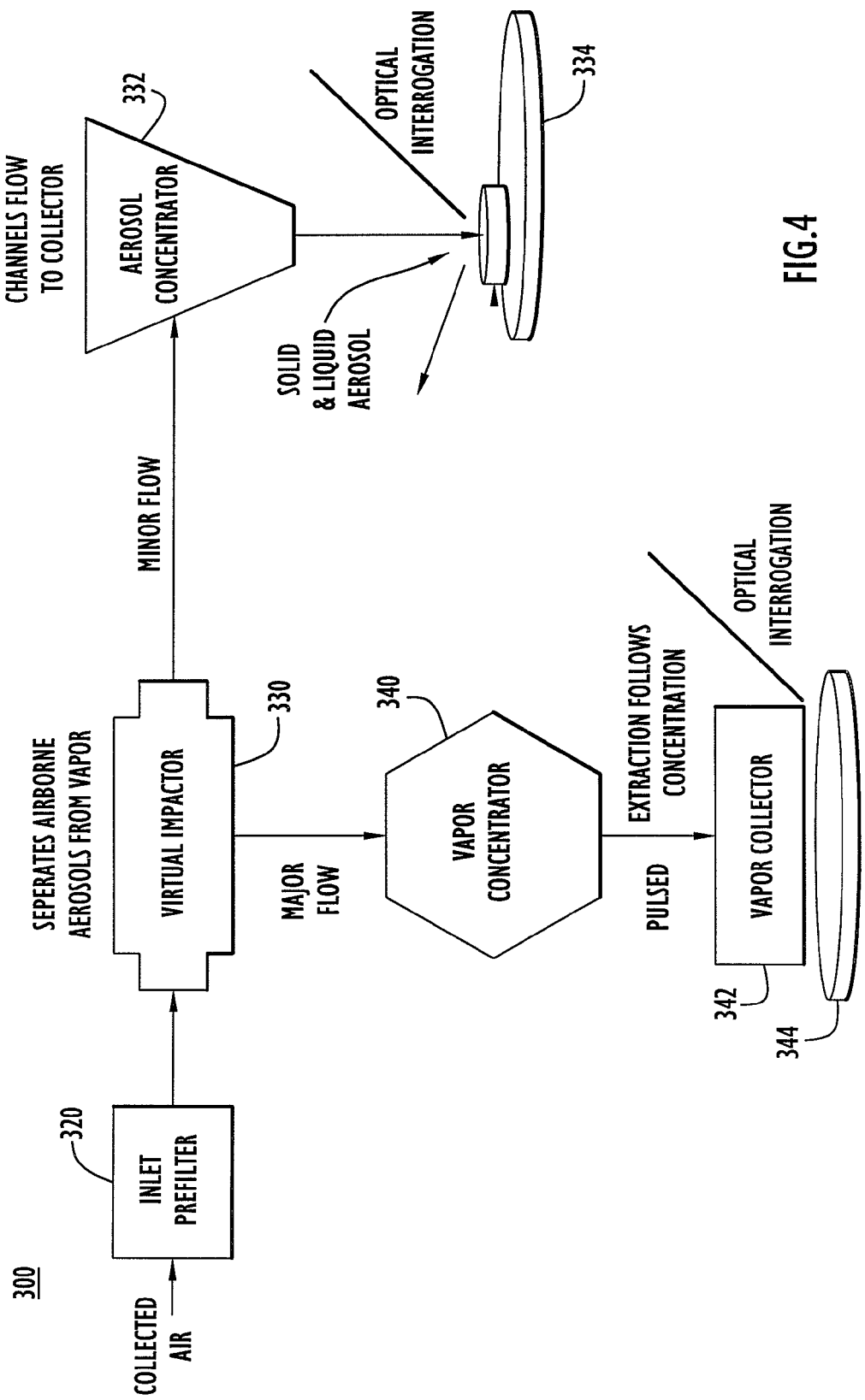
FIG. 4 is a block diagram of the air sampler unit according to one embodiment of the invention.

Referring now to FIGS. 3 and 4, the air sampler 300 is shown in more detail. The air sampler 300 comprises a body or housing 310 having an intake port 312 and an exhaust port 314. The intake port 312 draws in air and any airborne (aerosol) particles or vapor in the air. To this end, one or more pumps and a motor driven blower fan (not shown) may be provided in the housing 310 to draw air through the intake port 312 and pass exhaust to the exhaust port 314. There is an interrogation port 316 that provides optical access to the interior of the body 310 for purposes described hereinafter.

Within the air sampler 300, there is an inlet prefilter 320 through which collected air passes. The output of the inlet prefilter 320 is coupled to a virtual impactor 330. The inlet prefilter 320 is a mechanical device that acts like a self cleaning filter to prevent larger particles from entering the housing 310 and interfering with operation of the virtual impactor 330. One output flow of the virtual impactor 330 goes to an aerosol concentrator 332, and the other output flow goes to a vapor concentrator 340. The aerosol concentrator 332 directs collected aerosol particles onto a collection surface on a carousel 334 for optical interrogation. Similarly, the vapor concentrator 340 concentrates vapor to a vapor collector 342 which condenses vapors on collection surface of a carousel 344 for optical interrogation. In one embodiment, the air sampler 300 may include only aerosol capturing capability for certain applications, in which case the vapor concentrator 340, vapor collector 342 and carousel 344 would not be provided.

The virtual impactor 330 is a device that sorts the aerosol particles out of the sampled air and directs those particles to the aerosol concentrator 332. Not by way of limitation, the virtual impactor 330 may be a MicroVIC® Particle Concentrator, manufactured by MesoSystems Technology, Inc. The aerosol concentrator 332 directs the aerosol particles (solid or liquid) through an impaction nozzle and to the carousel 334. For example, the Micro VIC® is equipped with impaction nozzles that perform the function of the aerosol concentrator 332. Thus, in one embodiment, a single device may perform the functions of the virtual impactor 330 and the aerosol concentrator 332.

The carousel 334 comprises a surface or collection media on which particles separated from the collected air are directed by the aerosol concentrator 332. As shown in FIG. 4, the carousel aerosol collection surface is, for example, a disk or a plate shaped device. The aerosol cloud is accelerated through the aerosol concentrator 332 and directed at the carousel 334. The aerosol particles, due to their inertia, impact directly on the carousel 334.

The carousel 334 continues to collect the particles until there is an amount sufficient for interrogation. In one embodiment, the carousel 334 rotates the collected particles to position to be illuminated by a laser while aerosol particles are collected on a different portion of the carousel 334. For example, the carousel 334 may comprise a disk-shaped surface onto which particles separated from collected air are impacted or concentrated at one position of the disk, while particles previously collected and concentrated onto another position of the disk are illuminated by a laser. The disk is rotated for each new collection cycle. After collected particles are interrogated by a laser, they may be offloaded from the carousel 334 and stored in the sample storage container for further analysis at a later point in time. This allows a user to perform additional confirmatory and forensic test on aerosol samples or threats.

The other output flow from the virtual impact goes to the vapor concentrator 340. Many technologies are known for performing the function of the vapor concentrator 340. Two examples of suitable devices are the "Mesochannel" gas sampler (MGS) concentrator, developed by MesoSystems Technologies, Inc., with U.S. government support; and a version of the Cascade Avalanche Sorbent Plate Array (CASPAR) concentrator developed at the U.S. Naval Research Laboratory, but commercially available.

Vapor concentration by either an MGS type device or a CASPAR type device is allowed to continue until the minimum amount of air is processed through the device to build the concentration level, as dictated by a complete signature analysis of the designated list of substances of interest. After a vapor has been concentrated, the adsorbed molecules are desorbed on the vapor collector 342.

There are several methods of collecting the concentrated vapor for Raman interrogation, including without limitation, a cold plate, a micro porous surface or a vacuum cell. A cold plate design is based on the principle that if a vapor impinges on a cold surface, the vapor condenses to yield a liquid. This liquid can then be interrogated using a Raman-based detection system as described above for collected aerosol particles. In one embodiment, cooling the cold plate may be done with an integral thermal electric cooler (TEC). Collecting water vapor can be minimized using dry air in the desorption step of the vapor concentrator. The cold plate may be cleaned by applying heat to it to drive off the liquid.

Figure 5A:
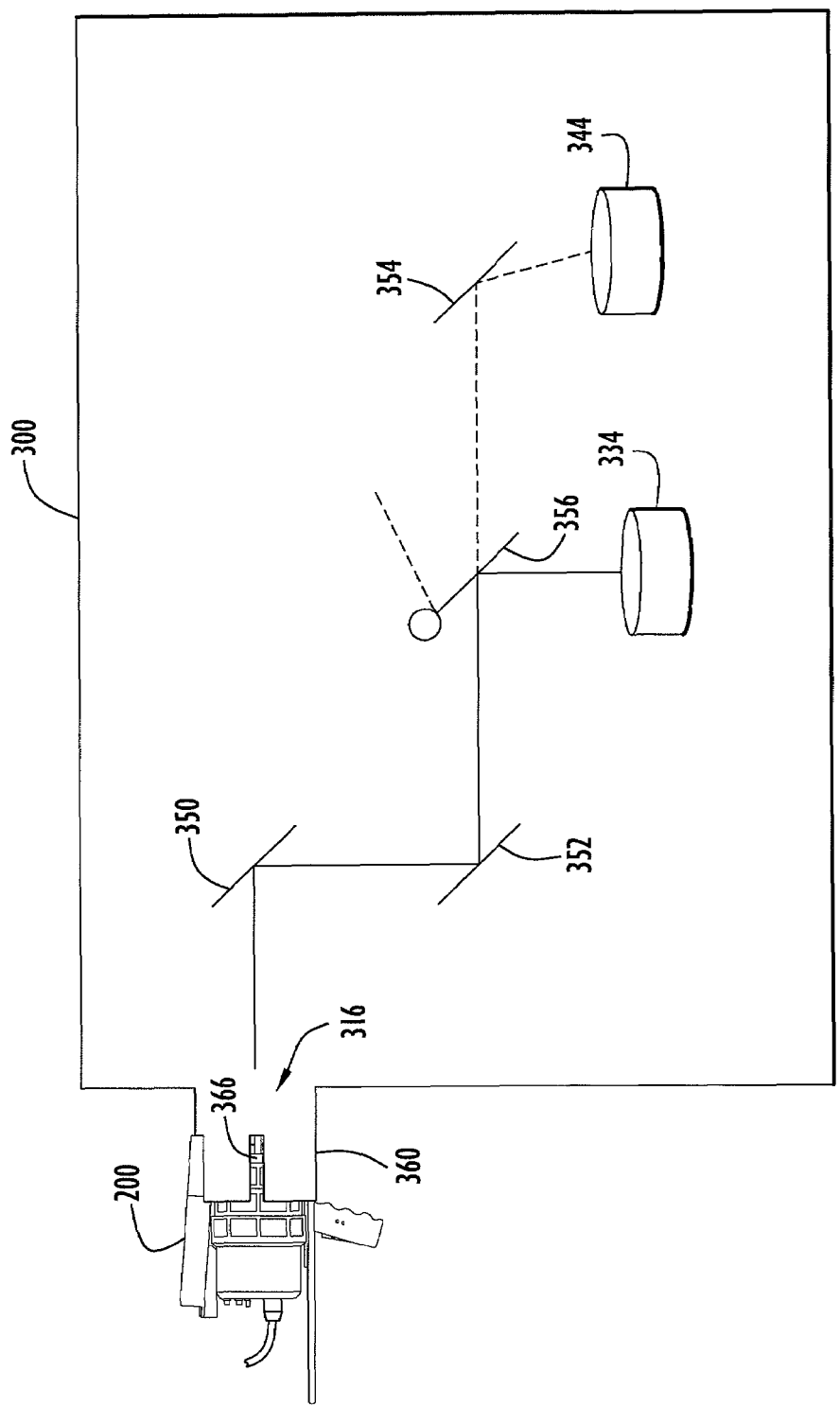
FIG. 5A is a schematic diagram showing the optical devices in the air sampler unit and a support to removably support a hand-held unit according to an embodiment of the invention.

Turning to FIG. 5A, a schematic diagram of the interior of the air sampler 300 is shown. Inside the air sampler 300, there are fixed optical elements (e.g., mirrors) 350, 352 and 354 and an optional movable optical element (e.g., flipper mirror) 356. The function of the optical elements 350, 352, 354 and 356 is to provide a bi-directional optical path between the interrogation port 316 and the aerosol carousel 334, or between the interrogation port 316 and the vapor carousel 344. The movable optical element 356 is moved between one of two positions, wherein in one position, it completes an optical path with the carousel 334 and, in another position, it completes an optical path with the carousel 344. In the event that the air sampler 300 is designed to capture aerosol particles only, the movable optical element 356 is not necessary and only one or more fixed optical elements may be needed to complete an optical path with the aerosol carousel 334.

According to an embodiment of the invention, the air sampler 300 has a holster or support mount/structure 360 positioned at the interrogation port 316 to removably receive and support the hand-held unit 200 in position and alignment with optical components. In this way, the optical interrogation components contained inside the hand-held unit 200 can be used to interrogate collected aerosol particles or vapor-sourced particles inside the air sampler 300.

The holster 360, shown in greater detail in FIG. 5B, comprises a cylindrical hollow body having a first length portion that attaches to the housing of the air sampler 300 and a second length portion 364 that receives the hand-held unit 200. The second length portion 364 comprises slots 366 that are designed to receive a certain external structure of the hand-held unit 200 to ensure proper alignment/orientation of the hand-held unit 200 therein for interaction with the optical components inside the housing of the air sampler 300. The slots 366 are one example of registering the hand-held unit 200 with the air sampler 300. Other complementary structures on the hand-held unit 200 and the air sampler 300 may be used.

Thus, according to one aspect of the invention, an air collector unit is provided that comprises a housing, a virtual impactor or other device contained in the housing that separates aerosol particles in collected air, a collection surface on which particles separated from collected air by the virtual impactor are collected, an opening in the housing, and a support structure on the housing that is suitable for removably supporting an interrogation unit so as to permit the interrogation unit (hand-held unit 200) to illuminate the collection surface and capture scattered optical energy from the collection surface.

Figure 6:
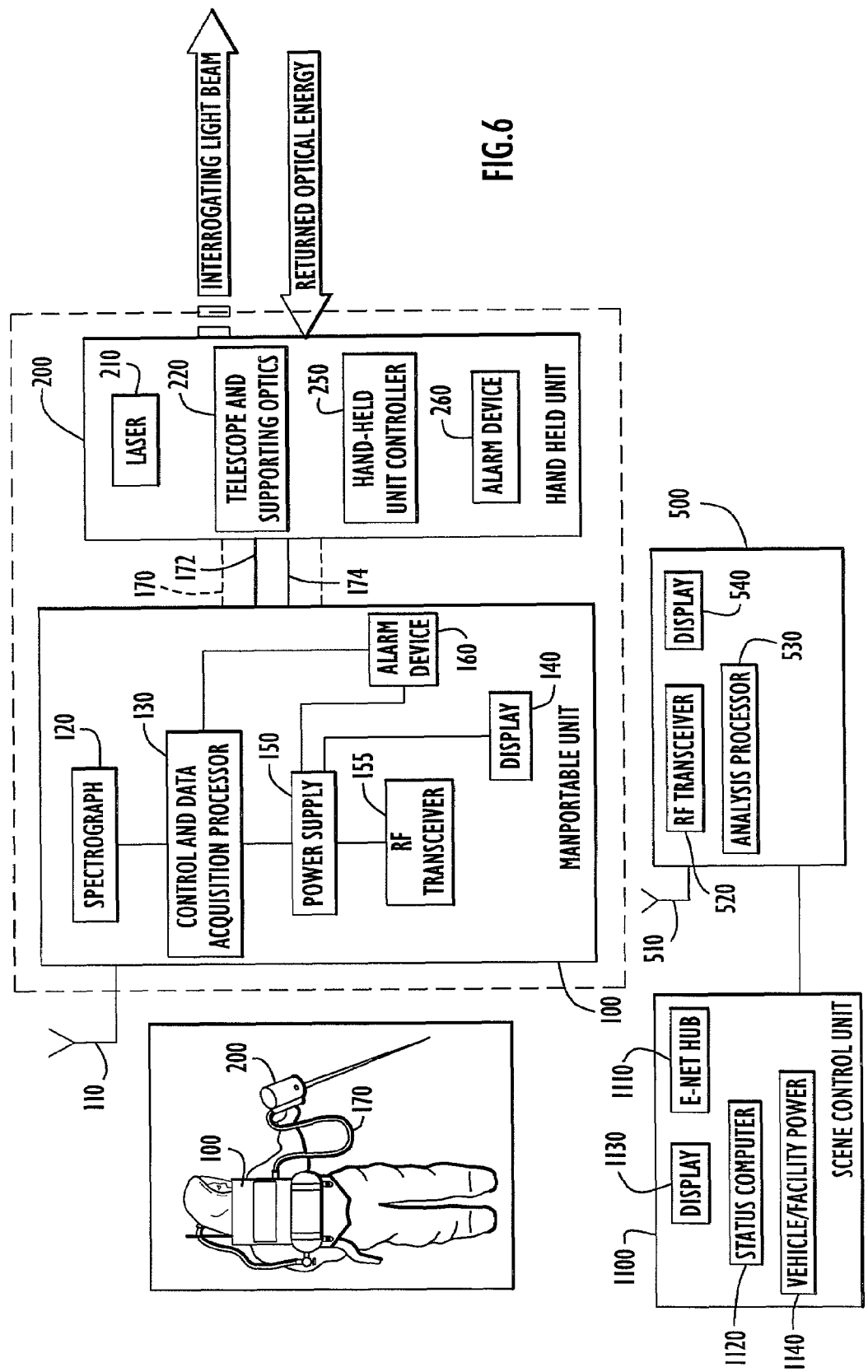
FIG. 6 shows a block diagram of a manportable unit, control unit and scene control unit of the system according to an embodiment of the invention.

Turning now to FIG. 6, the manportable unit 100 and hand-held unit 200 are described in greater detail. The manportable unit 100 comprises a spectrograph 120, a control and data acquisition processor 130, a display 140, a power supply 150, a radio frequency (RF) wireless transceiver/modem 155 for supporting wireless communication via antenna 157 and an alarm device 160. The power supply 150 supplies power for the components in the manportable unit 100 as well as for some components in the hand-held unit 200. The display 140 may be a snap-on or flip-down display mechanism viewable by the operator, or a display visible on a visor, such as a heads-up display. The display 140 can be used to display information to the user concerning the detection of hazardous substances.

In one embodiment, the spectrograph 120 comprises a light dispersing element and a detector. The light dispersing element may be a diffraction grating or prism and the detector may be an intensified charge coupled device (ICCD), for example. The light dispersing element uses dispersive optics to separate the constituent wavelengths (colors) of the light directed to it and directs the dispersed light onto the detector. The detector detects the light intensity at each of a plurality of wavelength "bins" and produces a signal or digital data that representative thereof. The processor 130 may be a computer, digital signal processor, programmable microcontroller or other computing device that analyzes the spectrum data produced by the spectrograph 120. The processor 130 uses a stored library of known spectra and attempts to match the measured spectra (produced by the spectrograph 120) with the library spectra so as to identify a substance in the collected and sampled particles or substances. The results of the analysis may then be supplied to the transceiver 90 for transmission to a remote device for further study or for informational purposes. The transceiver 155 may receive commands from a remote controller or device and in response transmit reports concerning the substances on an interrogated surface. The transceiver 155 may employ wired communication techniques or wireless (e.g., radio frequency) communication techniques via antenna 157. In an alternative embodiment, the manportable unit may transmit the spectrum data it produces to a remote device, (i.e., the control unit 500) for analysis.

The processor 130 may be a computer containing memory in which one or more programs are stored that cause the computer to perform various spectroscopy analysis algorithms and control procedures. In particular, when the manportable unit 100 and the hand-held unit 200 are used to interrogate a surface away from the vehicle (while carried by a person), the processor 130 may perform a full analysis of the spectrum data produced by the spectrograph 120, or it may be perform a fast first level analysis and then send the unprocessed or preprocessed spectrum data to a remote unit for more in depth processing of the spectrum data. The alarm device 160 in the manportable unit 100 produces an audible and/or visual alert notification when activated. The alarm device 160 may be integrated into the display 140.

The hand-held unit 200 is connected by an umbilical cable 170 to the manportable unit 100. The hand-held unit 200 is held in the hand of a user and is used to emit a light beam onto a surface to analyze with spectroscopy techniques a substance in solid or liquid phase on a surface in order to determine a composition of the substance. The substance may be a hazardous substance or contaminant, such as a chemical, biological or explosive substance on the ground, floor, wall or other objects. Generally, the hand-held unit 200 is used to interrogate a suspected surface at a stand-off distance of approximately one meter, and to return spectrum related data about the threat to the manportable unit 100 that analyzes the spectrum related data, determines whether there is a presence of a harmful threat, and rapidly issues a notification of the type of threat, e.g., in less than a second. In addition, according to one aspect of the present invention, the hand-held unit 200 may also be used to interrogate particles obtained from air samples by the air sampler 300 when it is placed in the holster 360 of the air sampler 300.

The hand-held unit 200 comprises a laser light source 210, telescope and supporting collection optics 220 and a controller 250. The laser light source 210 emits an interrogating light beam and the telescope and supporting optics 220 capture the returned optical energy and direct that energy over the umbilical 300 to the spectrograph 120 in the manportable unit 100. The controller 250 controls operation of the laser 210 in response to commands received from the manportable unit 100. The hand-held unit 200 may also comprise an alarm device 260 similar to alarm device 160 in the manportable unit 100.

The cable 170 comprises a fiber optic bundle 172 to couple the optical energy captured by the hand-held unit 200 to the spectrograph 120 in the manportable unit 100. The cable 170 also comprises at least one electrical conductor 174 (and more likely a plurality of electrical conductors) used to communicate commands from the manportable unit 100 to the hand-held unit 200 and other data from the hand-held unit 200 to the manportable unit 100.

The laser 210 in the hand-held unit generates an interrogating light beam directed at a surface of interest. The telescope and supporting optics 220 capture returned optical energy from the surface of interest. The light beam may any suitable type of light that is useful for analyzing characteristics of a liquid and/or solid substance on a surface. For example, the laser 210 may produce an ultraviolet (UV) laser beam, such as an Nd:YAG or Nd:YLF laser. Moreover, the laser 210 may produce beam of light such that the returned optical energy consists of Raman scattered optical energy that is analyzed using spectroscopy techniques. Associated with the laser 210 there may also be visual range finding optics for focusing the light beam at stand-off distances onto the surface of interest.

The manportable unit 100 may be in communication with the control unit 500 by wired or wireless link. In the control unit 500, there is an RF transceiver 520, an analysis processor 530 and a display 540. The control unit 500 may coordinate operations of the manportable unit 100 and the vehicle-mounted sensor 400. The analysis processor 530 may be used to perform spectral analysis on the spectrum data produced by the manportable unit 100 when the hand-held unit 200 is interrogating a surface in the air sampler 300. However, it is also possible that the processor 130 in the manportable unit 100 may process the spectrum data produced when the hand-held unit 200 interrogates a surface in the air sampler 300. In addition, the analysis processor 530 may be used to perform analysis on the spectrum data obtained by the vehicle-mounted sensor unit 400.

The control unit 500 may be in further communication with a scene control unit or station 1100. The scene control unit 1100 may include a network interface, such as an Ethernet hub (E-Net hub) 1110, a status computer 1120, a display 1130 and a power supply 1140. The scene control unit 1110 may be operated by a commander on the scene, for example, whose responsibility it is to coordinate activity with respect to actual or potential detection of a hazardous substance.

Figure 7:
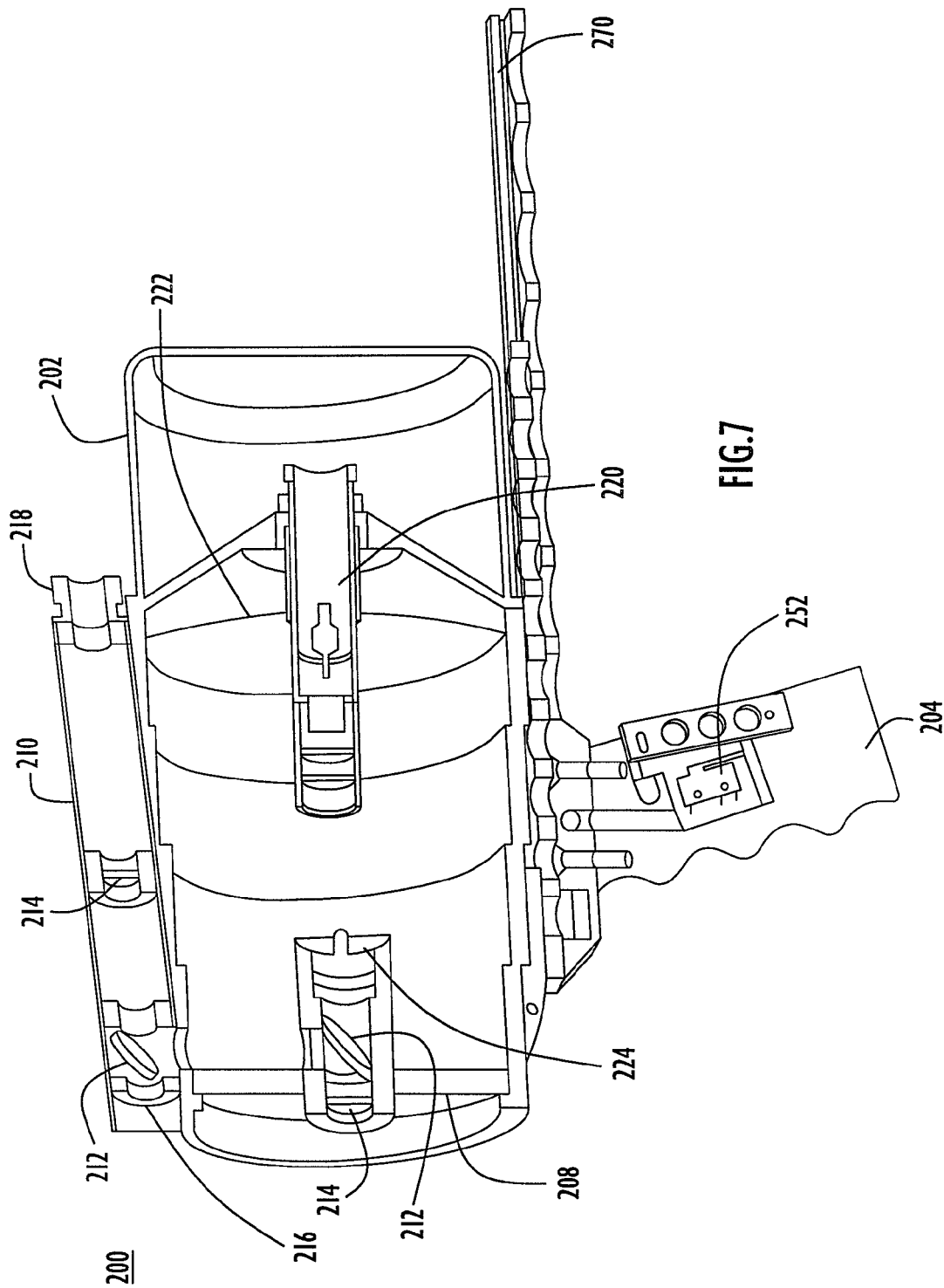
FIG. 7 is a perspective view of a hand-held unit according to one embodiment of the invention.
Figure 9:
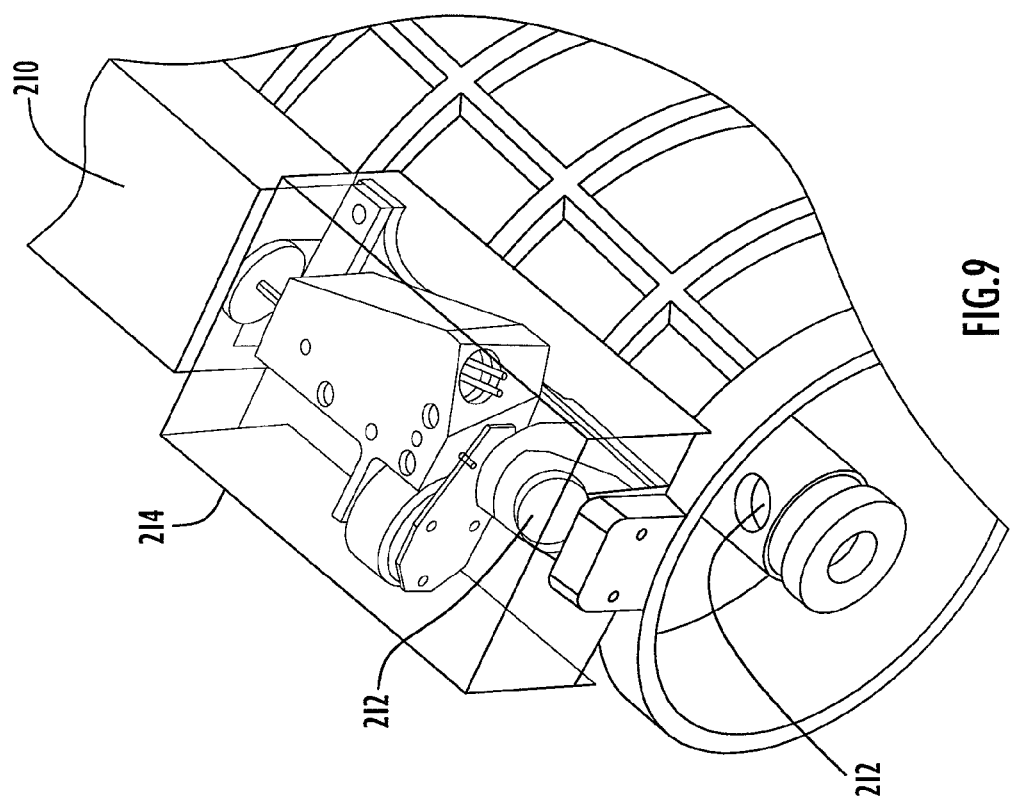
FIG. 9 is a top view of the hand-held unit according to one embodiment of the invention.
Figure 8:
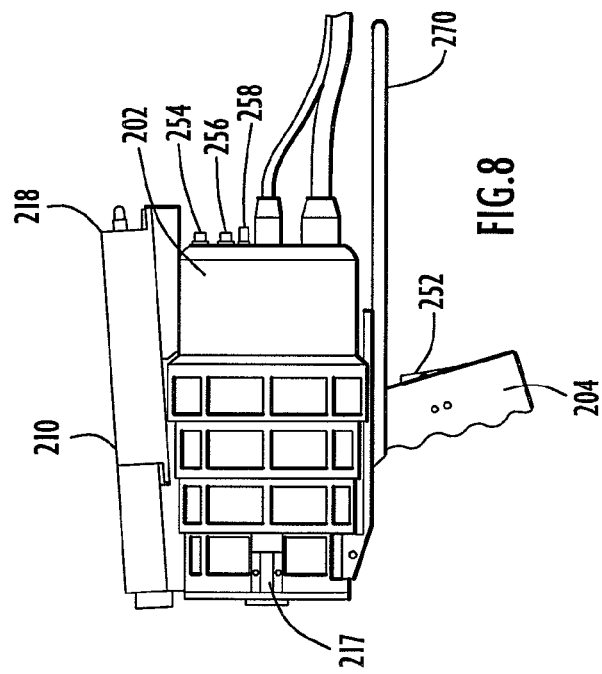
FIG. 8 is a side view of the hand-held unit according to one embodiment of the invention.

Turning to FIGS. 7-9, the hand-held unit 200 is described in more detail. In one embodiment, the hand-held unit 200 may comprise a main housing 202 and a hand-grip portion 204. The housing contains the controller 230 and related hardware and also serves as a support for the laser 210. The laser 210 is mounted on the top of the housing 202 and includes fold mirrors 212 and focusing optical elements 214 that permit the laser 210 to be emitted co-linearly with the boresight of the collection telescope. There is a laser power meter 216 that receives a small fraction of the laser light via one of the fold mirror 212 to permit monitoring of the laser power being transmitted. There is an articulated arm connection 218 associated with the laser 220 that can tip and tilt the optical axis of the laser beam. The fold mirrors 212 can tip or tilt to adjust the optical path of the laser beam. The housing 202 has a front window 208 sized to support the optical elements associated with the laser 210 and the telescope 220 thereby eliminating the need for spider supports that would otherwise interfere with detection of Raman backscatter. The supporting optics for the telescope 220 comprises a fixed primary mirror 222 and a movable secondary mirror 224. The secondary mirror 224 can tip and tilt to adjust the optical path for the returned optical energy through the telescope 220. The telescope 220 focuses any reflected backscattered (e.g., Raman) light into the fiber optic bundle 172 that is connected to the hand-held unit 200 and that in turn delivers the returned optical energy to the spectrograph 120 contained in the manportable unit 100 (FIG. 2).

According to one embodiment, to obtain UV wavelength laser light, a 1047 nm light beam is twice frequency doubled and includes an optical network is provided that separates the three wavelengths generated to produce the desired UV laser light to the output for transmission. Details of such the frequency-doubling optical network are not provided herein because such techniques are known in the art.

There is a cover 219 that fits over the back of the housing 202 to protect the controller 250 and related components. In addition to the handle or grip 204 there is an elongated arm 270 on which a user may place another hand to assist in holding the unit 200.

On opposite sides of the housing 202 there are focusing diodes 217 that are used to assist the user in manually keeping the hand-held unit 200 at the proper focal distance from the surface being interrogated. The diodes 217 are angled inward with respect to each other such that the beams they emit intersect on the surface at a predetermined distance from the hand-held unit 200, e.g., approximately one meter. The point of intersection corresponds with the optimum focus distance of the telescope 220.

As shown in FIG. 8, there is a "dead-man's" switch 252 on the handle or grip 204 and there are two switches 256 and 258 located on the back of the unit 200 as shown in FIG. 5. To make the hand-held unit 200 operational, these three switches are actuated in order. Specifically, after a software operation at the manportable unit 100 enables the system, the switch 252 on the handle 204 is first actuated to close an operating circuit. Next, switch 256 on the back of the hand-held unit 200 is actuated to turn on the focusing diodes 217. Finally, the switch 258 is actuated to turn on the laser 210 or open a physical shutter on the device 200 that permits the laser light to be emitted. One or more lights (e.g., LEDs) 254 on the back of the unit 200 may be provided to indicate whether the unit is on and operational.

Figure 10:
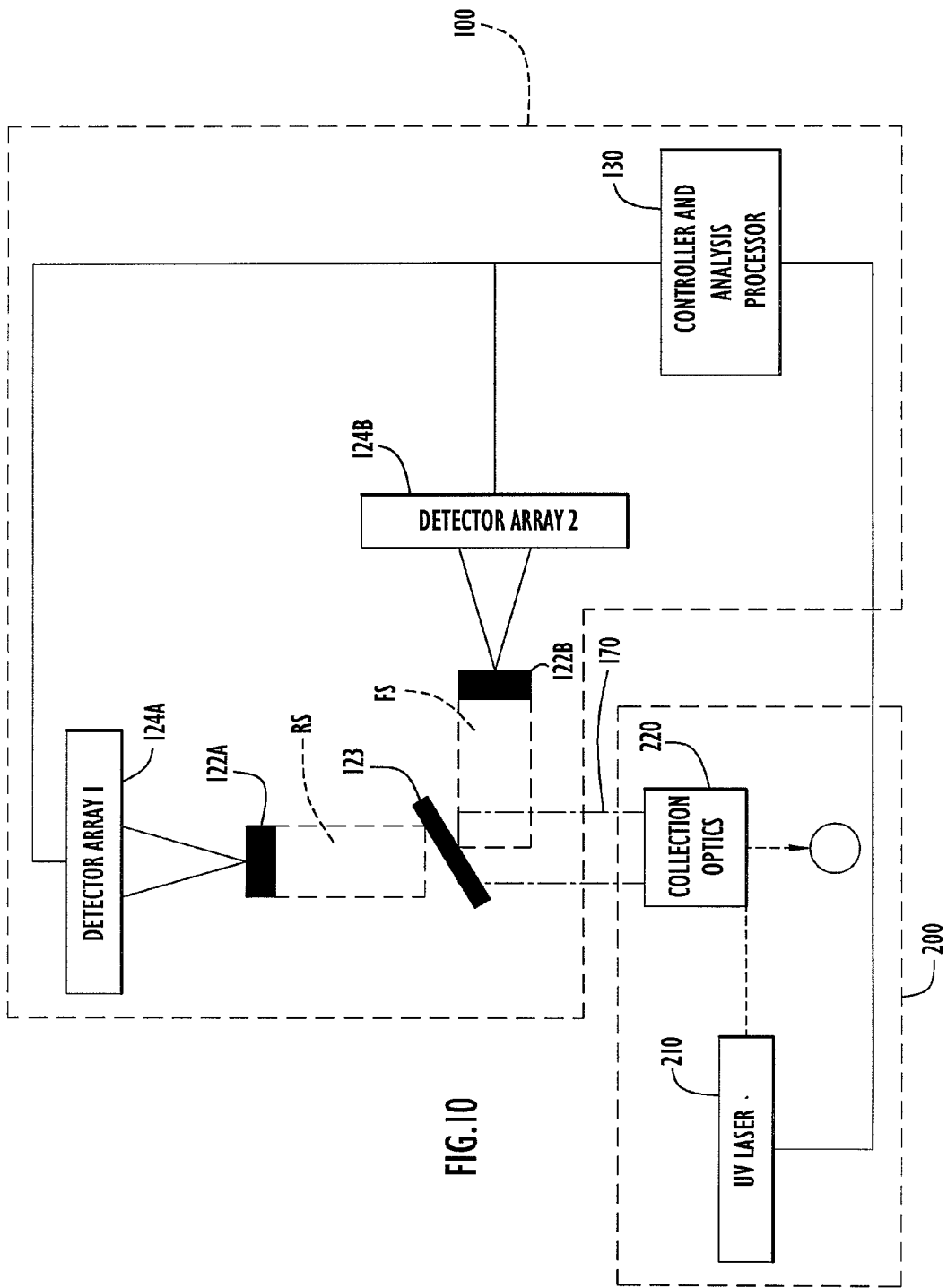
FIG. 10 is a block diagram showing a spectrograph in the manportable unit according to an alternative embodiment of the invention.

Turning to FIG. 10, another embodiment of the invention is described. In this embodiment, the spectrograph 120 in the manportable unit 100 is modified to simultaneously collect Raman scattering and fluorescence scattering in response to UV illumination of a surface, such as a collection surface in the air sampler 300. The UV illumination is in the "deep" UV wavelength region (less than 263 μm) so that the Raman scattering and the fluorescence scattering are in different wavelength regions. To this end, there are two light dispersing elements 122A and 122B and a wavelength selective optical element 123. The wavelength selective optical element 123 separates the Raman scattering from fluorescence scattering since they are in two different wavelength regions. By way of example only, the wavelength selective optical element 123 is a dichroic mirror, tunable bandpass filter or reflective Kerr medium capable of directing Raman scattering RS in a first wavelength region to the first light dispersing element 122A and directing fluorescence scattering FS in a second wavelength region to a second light dispersing element 122B. For example, the Raman scattering is in a first wavelength region extending 263 nm to 284 nm and the fluorescence scattering is in a second wavelength region extending from 284 nm to 550 nm. The light dispersing element 122A separates out the constituent wavelengths of the Raman scattering and directs those wavelengths of light to a detector 124A. The light dispersing element 122A separates out the constituent wavelengths of fluorescence scattering and directs those wavelengths of light to a detector 124B.

The first detector 124A detects the light intensity at each of a plurality of wavelength bins and produces a signal or Raman digital data that represents the Raman scattering. The second detector 124B detects the light intensity at each of a plurality of wavelength bins and produces a signal or fluorescence digital data that represents the fluorescence scattering. By way of example, the first detector 124A may be a gated detector array such as an ICCD that converts the incoming spectra to digital data. Similarly, the second detector 124B is an ICCD, or an array of very fast gated photodiodes that can capture not only the shape of the fluorescence spectra but also the snapshots of the fluorescence spectra at multiple time instances over a time interval following a pulse or burst of a UV light beam for purposes of deriving the fluorescence lifetime at one or more detection wavelengths. Thus, Raman spectra and fluorescence spectra are simultaneously captured from a single pulse or burst of UV light, or average such data obtained as a result of each of several pulses of UV light.

The processor 130 can then analyze the Raman data and fluorescence data. Moreover, the processor 130 may compute fluorescence lifetime data at one or more detection wavelengths from fluorescence data obtained from the second detector 124B at each of the plurality of time instances (hereinafter referred to as the "fluorescence samples") over the time interval following the UV light beam pulse or burst. Thus, the data processor may analyze the Raman spectra, fluorescence spectra and fluorescence lifetime at one or more wavelengths to characterize or identify substances. Alternatively, the manportable unit 200 may transmit the Raman data and fluorescence data to the control unit 500 wherein the processor 530 may perform the analysis on the Raman and fluorescence data.

Heretofore, it is not known to use Raman for detecting non-fluorescing substances. By using "deep" UV laser light, the Raman scattering will be in a different wavelength region than that of the background noise (e.g., fluorescence spectrum). As a result, the signal-to-interference ration (S/I) is relatively strong. These techniques can be used to continuously monitor particles extracted from collected air. The UV light employed by the techniques described herein will not degrade the interrogated particles.

Figure 11:
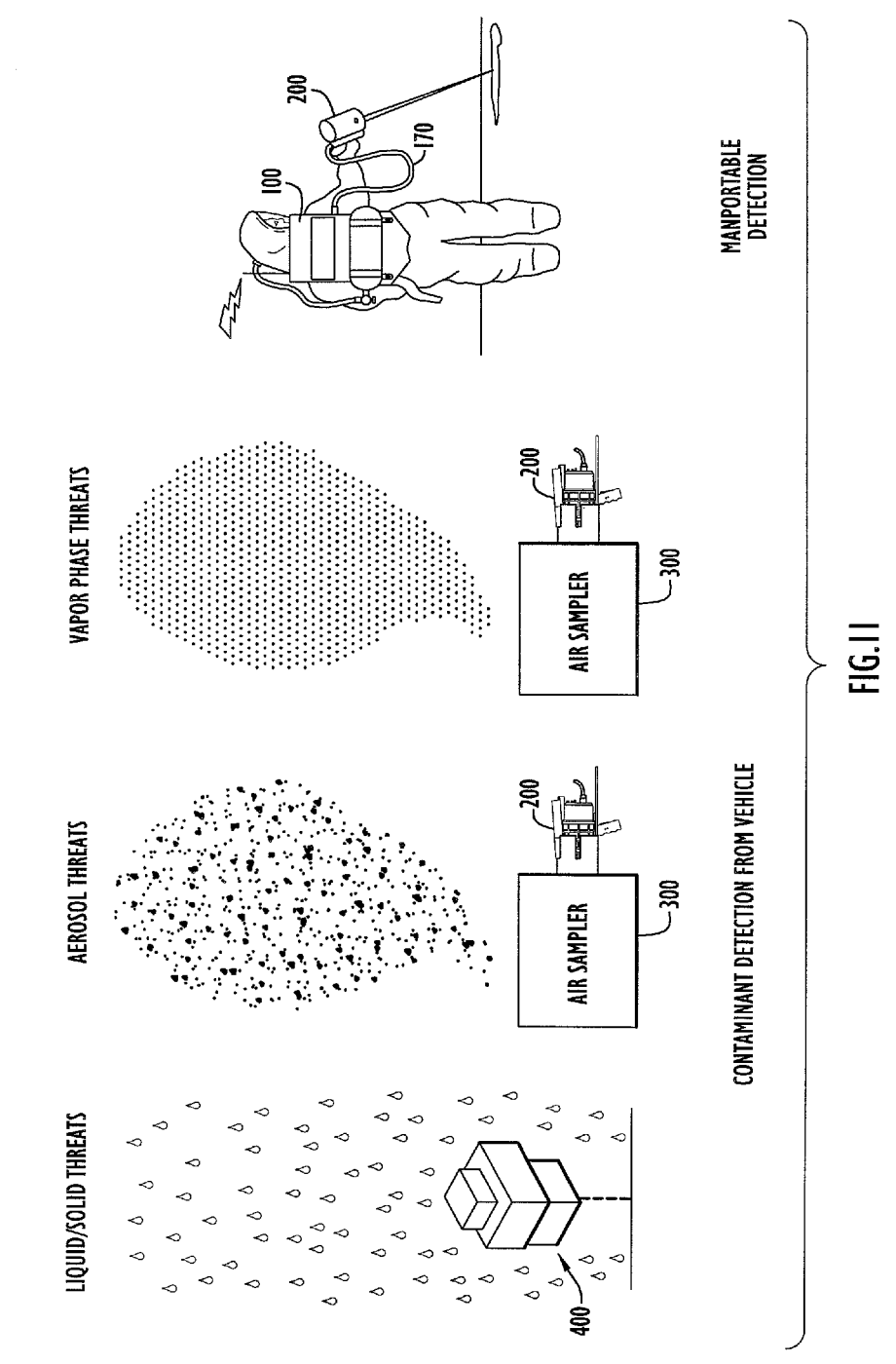

FIG. 11 illustrates the various capabilities of the system 10 according to embodiments of the invention. As indicated above, the system 10 is mounted on a vehicle and may be operated while the vehicle is moving. For example, the vehicle-mounted sensor 400 may be operated to monitor the ground surface for liquid or solid threats and/or the hand-held unit 200 may be installed in the holster of the air sampler 300 to interrogate aerosol particles or vapor-sourced particles associated with any potential airborne contaminants. In addition, the manportable portion of the system may be deployed off of the vehicle to allow a person to scan the ground surface away from the vehicle and report back to the control unit on the vehicle as to any detected contaminants.

The spectroscopy techniques described herein do not require targeting. Targeting involves locating a particle of interest through highly complex algorithms that nearly always require human intervention or confirmation, and then subsequently "zooming" in on a particle of interest for more detailed analysis. Thus, targeting techniques do not allow for continuous monitoring, such as continuous monitoring of collected air. Furthermore, the techniques of the present invention do not rely on fluorescing or auto-fluorescing whereas prior art spectroscopy techniques for biological substances only use fluorescence analysis and therefore would not be able to detect non-fluorescing biological substances.

There are numerous other advantages of the detection system and methods described herein. The system is comprised of multiple modules that use a common technology and common analysis electronics/software. For example, and not by way of limitation, the control unit 500 may include the processing algorithms needed to process spectrum data produced by the vehicle-mounted sensor unit 400 and the manportable unit 100 when interrogating particles obtained by the air sampler 300. That is, the processor 530 in the control unit 500 is used to analyze Raman data (produced by the spectrograph in the manportable unit 100) to detect a non-fluorescing substance and to analyze fluorescence data (also produced by the spectrograph in the manportable unit 100) to detect a fluorescing substance. The manportable unit 100 need only include the processing algorithms needed to perform first level fast analysis of spectrum data when the manportable unit 100 and hand-held unit 200 are deployed by a user away from the vehicle. This reduces the number of components, and thus cost, for a system having both vehicle-mounted detection functions and manportable detection functions. The system has on-the-move non-contact detection capabilities afforded by the vehicle-mounted sensor. In addition, the system is capable of detecting fluorescent and non-fluorescent aerosol substances from collected air samples. The system also has manportable vehicle-dismounted surveillance capabilities for surface substances afforded by the manportable unit in conjunction with the hand-held detection unit.

The system and methods described herein may be embodied in other specific forms without departing from the spirit or essential characteristics thereof. The foregoing embodiments are therefore to be considered in all respects illustrative and not meant to be limiting.

What is claimed is:

1. A detection system, comprising:
   a hand-held unit comprising a light source configured to optically interrogate a surface and collection optics configured to capture scattered optical energy from the surface;
   a manportable unit connected to said hand-held unit and configured to receive said scattered optical energy captured by the hand-held unit, comprising a spectrograph that is configured to convert said scattered optical energy to spectrum data and a computing device that is configured to analyze the spectrum data produced by the spectrograph in the manportable unit; and
   an air collector unit that is configured to collect air and to separate particles in the collected air for deposit onto a collection surface, wherein the air collecting unit comprises a port configured to permit optical access to said collection surface by said hand-held unit and a support structure configured to removably support said handheld unit in a position for optical interrogation of said collection surface;

wherein the hand-held unit is configured to be removable from said air collector unit to permit the manportable unit and the hand-held unit to be carried away from the air collector unit for use as an integrated portable detection system by a user.

2. The system of claim 1, wherein the air collector unit comprises a housing having an intake port configured to collect air and a virtual impactor in said housing configured to separate particles in the collected air.

3. The system of claim 2, and further comprising a vapor collector connected to said virtual impactor that extracts particles from vapor in the collected air.

4. The system of claim 1, wherein the light source in the hand-held unit comprises an ultraviolet laser light source that directs a beam of ultraviolet light that is suitable for exciting Raman scattering.

5. The system of claim 4, wherein the ultraviolet laser light source is suitable for further exciting fluorescence scattering, and wherein the Raman scattering and the fluorescence scattering are in different wavelength regions.

6. The system of claim 4, wherein the hand-held unit comprises a wavelength selective optical element that separates the Raman scattering and the fluorescence scattering.

7. The system of claim 5, wherein the spectrograph in the manportable unit comprises first and second light dispersing elements and first and second detectors, wherein the first light dispersing element disperses the Raman scattering into its constituent wavelengths and the first detector generates Raman data from light directed to it by the first light dispersing element, and the second light dispersing element disperses the fluorescence scattering into its constituent wavelengths and the second detector generates fluorescence data from light directed to it by the second light dispersing element.

8. The system of claim 6, and further comprising a control unit connected to said manportable unit, wherein the control unit comprises a computing device that analyzes the Raman data to detect a non-fluorescing biological substance and analyzes the fluorescence data to detect a fluorescing substance.

9. The system of claim 1, and further comprising a control unit coupled to said manportable unit and said air collector unit, and wherein the control unit comprises a computing device that analyzes the spectrum data.

10. The system of claim 8, wherein the air collector unit is mounted to a vehicle.

11. The system of claim 9, and further comprising a vehicle-mounted sensor unit on the vehicle and connected to said control unit, wherein the vehicle-mounted sensor unit comprises a spectroscopy subsystem that interrogates a surface outside the vehicle while the vehicle is moving to produce spectrum data from the surface outside the vehicle.

12. The system of claim 10, and further comprising a cable that connects the hand-held unit to said manportable unit.

13. A vehicle-based detection system that also has manportable functions, comprising:

a vehicle-mounted sensor unit comprising a spectroscopy subsystem that is configured to direct light onto a surface outside the vehicle and to capture scattered optical energy from the surface outside the vehicle while the vehicle is moving;

a hand-held unit comprising a light source that is configured to emit a light beam onto a surface to be analyzed for presence of a substance, and collection optics that is configured to capture scattered optical energy from said surface;

a manportable unit connected to said hand-held unit and configured to receive said scattered optical energy captured by the hand-held unit, comprising a spectrograph that is configured to convert said scattered optical energy to spectrum data and a computing device that is configured to analyze the spectrum data produced by the spectrograph in the manportable unit; and a vehicle-mounted air collector unit that is configured to collect air and to separates particles in the collected air onto a collection surface, wherein the air collecting unit comprises a port to permit optical access to said collection surface by said hand-held unit and a support structure that is configured to removably support said hand-held unit in a position so that the light source in the hand-held unit directs light onto said collection surface and the collection optics captures scattered optical energy from said collection surface;

wherein the hand-held unit is configured to be removable from said air collector unit to permit the manportable unit and the hand-held unit to be carried away from the vehicle-mounted air collector unit for use as an integrated portable detection system by a user.

14. The system of claim 13, wherein the air collector unit comprises a housing having an intake port to collect air and a virtual impactor in said housing that separates particles in the collected air.

15. The system of claim 13, wherein the light source in the hand-held unit is suitable for exciting Raman scattering and fluorescence scattering, wherein the Raman scattering and fluorescence scattering are in different wavelength regions.

16. The system of claim 15, wherein the hand-held unit comprises a wavelength selective optical element that separates the Raman scattering and the fluorescence scattering, and wherein the spectrograph in the manportable unit comprises first and second light dispersing elements and first and second detectors, wherein the first light dispersing element disperses the Raman scattering into its constituent wavelengths and the first detector generates Raman data from light directed to it by the first light dispersing element, and the second light dispersing element disperses the fluorescence scattering into its constituent wavelengths and the second detector generates fluorescence data from light directed to it by the second light dispersing element.

17. The system of claim 16, and further comprising a control unit mounted to the vehicle and connected by a wired or wireless link to said manportable unit, wherein the control unit comprises a computing device that analyzes the Raman data to detect a non-fluorescing biological substance and analyzes the fluorescence data to detect a fluorescing substance.

18. The system of claim 17, wherein the control unit is further connected to the vehicle-mounted sensor unit, and wherein the computing device of said control unit analyzes the spectrum data produced by the spectrograph in the vehicle-mounted sensor unit.

19. The system of claim 13, and further comprising a cable that connects the hand-held unit to said manportable unit.

20. A method comprising:

on a vehicle, collecting air into a housing;

separating particles in the collected air onto a collection surface in the housing;

providing a hand-held unit comprising a light source and collection optics;

removably supporting the hand-held unit with respect to an opening in the housing so as to align the light source and collection optics in the hand-held unit with respect to the opening;

activating the light source in the hand-held unit to illuminate a collection surface in the housing and to capture scattered optical energy from the collection surface;

removing the hand-held unit from the opening in the housing and carrying the hand-held unit away from the housing together with a manportable unit that is connected to the hand-held unit;

activating the light source in the hand-held unit to illuminate a surface away and outside from the housing;

capturing scattered optical energy with the hand-held unit and converting the scattered optical energy to spectrum data with a spectrograph in the manportable unit; and analyzing the spectrum data with a computing device in the manportable unit.

21. The method of claim 20, and further comprising analyzing the captured scattered optical energy from the collection surface of the housing with a computing device contained in a unit mounted on the vehicle.

22. The method of claim 20, wherein activating the light source in the hand-held unit to illuminate the collection surface in the housing comprises activating a laser light source in the hand-held unit so as to producing Raman scattering and fluorescence scattering from illumination of the collection surface in the housing.

23. An apparatus, comprising:

a housing;

a virtual impactor contained in said housing that separates particles in collected air;

a collection surface on which particles separated from collected air by the virtual impactor are collected;

an opening in the housing;

a hand-held interrogation unit comprising a light source configured to optically interrogate a surface and collection optics configured to capture scattered optical energy from the surface; and a support structure on the housing that is configured to removably support the hand-held interrogation unit so as to permit the hand-held interrogation unit to illuminate the collection surface and capture scattered optical energy from the collection surface;

wherein the hand-held interrogation unit is configured to be removable from the support structure to permit it to be carried away from the support structure for use as an integrated portable detection system by a user.

24. The apparatus of claim 23, wherein the support structure comprises a hollow body having a first length portion that attaches to the housing and a second length portion that is configured to receive the hand-held interrogation unit.

25. The apparatus of claim 24, wherein the second length portion of the support structure comprises one or more structures that are complementary to one or more structural features of the hand-held interrogation unit so as to orient the hand-held interrogation unit with the housing to ensure proper alignment and interaction with optical components inside the housing.

26. The apparatus of claim 24, wherein the second length portion comprises at least one slot that is configured to receive an external structure of the hand-held interrogation unit so as to orient the hand-held interrogation unit with the housing to ensure proper alignment and interaction with optical components inside the housing.

* * * * *

UNITED STATES PATENT AND TRADEMARK OFFICE
CERTIFICATE OF CORRECTION

| | | |
|---|---|---|
| PATENT NO. | : 7,636,154 B1 | Page 1 of 1 |
| APPLICATION NO. | : 11/614676 | |
| DATED | : December 22, 2009 | |
| INVENTOR(S) | : Howard N. LaValley et al. | |

It is certified that error appears in the above-identified patent and that said Letters Patent is hereby corrected as shown below:

Column 6, line 44, replace "a fall analysis" with -- a full analysis --; and

Column 12, line 12, replace "to separates particles" with -- to separate particles --.

Signed and Sealed this

Twenty-third Day of February, 2010

David J. Kappos
*Director of the United States Patent and Trademark Office*